United States Patent [19]

Dubin

[11] 4,090,977
[45] May 23, 1978

[54] OSMOTICALLY BALANCED ANTICOAGLANT

[75] Inventor: Stephen Dubin, Springfield, Pa.

[73] Assignee: Research Corporation, New York, N.Y.

[21] Appl. No.: 743,597

[22] Filed: Nov. 22, 1976

[51] Int. Cl.² ............................................ G01N 33/16
[52] U.S. Cl. .................. 252/408; 23/230 B; 195/1.8; 424/101
[58] Field of Search .................. 23/230 B; 260/534 E; 252/408; 195/1.8; 424/101

[56] References Cited

U.S. PATENT DOCUMENTS

| | | | |
|---|---|---|---|
| 3,449,414 | 6/1969 | Boettger | 260/534 E |
| 3,833,590 | 9/1974 | Dazzi | 260/534 E |
| 3,873,467 | 3/1975 | Hunt | 252/408 |
| 3,962,125 | 6/1976 | Armstrong | 23/230 B |
| 3,973,913 | 8/1976 | Louderback | 23/230 B |

OTHER PUBLICATIONS

Chemical Abstracts I, 66:44693 v (1967).
Chemical Abstracts II, 67:98781 m (1967).

*Primary Examiner*—Sidney Marantz
*Attorney, Agent, or Firm*—Haight & Huard

[57] ABSTRACT

An osmotically balanced anticoagulant mixture for the preservation of whole blood which comprises an admixture of the free acid form of EDTA, which raises hematocrit values, with a corresponding amount of a salt which lowers hematocrit values, preferably an alkali metal salt of EDTA, in ratios such that the hematocrit values are comparable to those of fresh or heparinized blood over a wide range of anticoagulant concentrations.

12 Claims, No Drawings

OSMOTICALLY BALANCED ANTICOAGLANT

BACKGROUND OF THE INVENTION

This invention relates to an improved anticoagulant composition for use with mammalian whole blood.

Hematological tests in human and veterinary medicine are employed for a host of diagnostic aids, and numerous blood anticoagulant mixtures have been widely employed to permit testing and measurement of whole blood properties without clotting. Citrate anticoagulants, the material of choice for blood banks and transfusion purposes, have never gained acceptance for hematological testing purposes. Oxalates are still used for hematological purposes but must be used rapidly and in fairly large quantities in order to avoid drastic influences on cellular morphology and distortion of hematocrit values. The coumadins, of great value as in vivo anticoagulants, are not suitable for in vitro applications due to the anticoagulating mechanism characteristic of these compounds. Heparin, although relatively expensive and unstable, is useful in blood gas analyses and ion concentration measurement due to its nonionic structure. However, although to a lesser extent than the oxalates, heparin also adversely affects the morphology and in particular the staining properties of white blood cells.

EDTA (ethylenediaminetetracetate) has today become the anticoagulant of choice for most routine hematology procedures. While the literature and product specifications are often unclear in using the designation EDTA as a generic term for the free acid and its various simple or complex (mixed) salts, normally with an alkali metal or a divalent alkaline earth metal cation, the potassium and sodium salts $Na_2$ EDTA and $K_3$ EDTA are at present most widely employed in this country.

For purposes of collecting blood samples to be used in hematological testing, anticoagulants are often pre-dispensed in evacuated collection tubes designed to draw a specified volume of a whole blood sample. In practice, the use of such tubes does not always entail collecting a full sample because of premature withdrawal, weakened vacuum or a number of other practical problems. Since very small quantities of blood are required for most hematology procedures, the sample will normally be adequate in terms of required volume and sent to the laboratory for testing anyway. The net effect of such occurrences results in a sample containing an excess concentration of anticoagulant over that which would be obtained by collecting a "full draft" sample. As shown in more detail hereinafter, variations in concentration of anticoagulants now employed can distort hematological test results. While perhaps not significant for many purposes, the distortion in lowering hematocrit values can be a serious matter for a patient or animal suffering dehydration, serious burns or the like and/or being prepared for treatment with an artificial kidney machine.

Hematocrit values are one of the most commonly employed hematological determinations. While the classic method for determining hematocrit has involved simple centrifugation of blood to which an anticoagulant has been added, electronic cell counters such as the Coulter Counter Model S have recently been employed. In the operation of this electronic cell counter, the blood is diluted 1:62,500 and a measured volume is drawn through an orifice while the electrical conductivity is measured between the two sides of the orifice. Cells have a lower conductivity than the diluting fluid. As they pass through the orifice, a change in conductivity occurs. The magnitude of the change is quantitatively related to the volume of the cells so that the MCV* can be determined. The packed cell volume (PCV) or hematocrit is then calculated as (MCV × RBC count)/10. While generally satisfactory, it has been found that discrepancies between centrifugally determined hematocrit values can be masked by such electronic cell counters. Since the presently employed EDTA salts act to lower hematocrit values this masking presents a real danger to a limited number of patients. Accordingly, there is a need for a blood anticoagulant composition which does not suffer the above mentioned deficiencies of prior art compositions.

* Mean corpuscular volume

OBJECTS OF THE INVENTION

Accordingly, it is a general object of the present invention to provide an improved anticoagulant composition and process for the preservation of whole blood.

Another object of the present invention is to provide an anticoagulant composition which exhibits substantially linear and reliable correlation between hematocrit values determined by electronic methods with those determined by centrifugation.

A further object of this invention is to provide an anticoagulant composition which has a minimal influence on hematocrit values over a wide range of concentration.

Still another object of this invention is to provide an anticoagulant composition using chemicals whose lack of toxicity is well established, and which is easily adapted for use with the blood from different mammalian species.

Other objects of this invention will become apparent to those skilled in the art to which the invention pertains by studying the present specification and claims.

SUMMARY OF THE INVENTION

Briefly, the above and other objects, features and advantages of the present invention are attained in one aspect thereof by providing an osmotically balanced anticoagulant for in vitro use with whole mammalian blood, which comprises an anticoagulantingly effective amount of a balanced EDTA salt composition consisting essentially of (a) $H_4$ EDTA and (b) a salt which lowers hematocrit values, the molar ratio of (a) : (b) being such that the hematocrit values of the blood sample are substantially identical to those of fresh or heparinized blood and substantially independent of the concentrations of (a) and (b).

DETAILED DISCUSSION

In accordance with the present invention, it has now been found that $H_4$ EDTA raises hematocrit values and accordingly can be used to offset the lowering of hematocrit values caused by other anticoagulant salts. The increase in hematocrit or packed cell volume which has now been noted with the addition of $H_4$ EDTA is quite unexpected. While not wishing to be bound by any theory of the invention, the Donnan theory of membrane equilibrium may be applied to explain the results. This requires that the relationship:

$$\frac{(H^+) \text{ plasma}}{(H^+) \text{ cells}} = \frac{(Cl^-) \text{ cells}}{(Cl^-) \text{ plasma}} = \frac{(HCO_3^-) \text{ cells}}{(HCO_3^-) \text{ plasma}}$$

be true and the assumption that the only cation present which can diffuse through the RBC membrane is $H^+$. When $H^+$ dissociates from $H_4$EDTA in the plasma, the ratio $(H^+)$ plasma/$(H^+)$ cells increases. The ratio $(HCO_3^-)$ cells/$(HCO^3-)$ plasma increases because more buffering base is available inside the cells. The $Cl^-$ of the plasma tends to pass into the cells in exchange for $HCO_3^-$ until the ratios are once again equalized at a new level. Since the ratio is a higher one, the number of osmotically active particles in the cells must now be higher than in the plasma. To equalize the osmotic pressure of the cells and plasma, water enters the cells and the RBC volume increases.

If, in fact, the changes in the PCV are osmotic, a mixture of two materials having equal and opposite osmotic effects should mitigate the variation. For example, 1 mg of $H_4$ EDTA and 8 mg of $Na_2$ EDTA have such effects and are adequate for prevention of clotting of 5 ml of blood. Such a mixture has been found to have minimal effects on the PCV of canine blood and to be substantially insensitive to concentration over a wide range.

The response of RBC volume to changes in osmotic pressure and the concentration of certain cations is well documented. In a previous study in our laboratories, the change in PCV in the presence of univalent cations such as $Na^+$, $K^+$, and $Li^+$ as a function of concentration was measured in multiples (1–10x) of the amounts computed to be dissociated from the recommended amounts of anticoagulant salts. In comparing these results to the effects of the anticoagulant salts, several complicating factors must be considered: (1) the removal from osmotic activity of $Ca^{++}$ and $Mg^{++}$ ions found in the plasma; (2) the osmotic activity of the EDTA moiety itself, (3) the dissociation constants of the anticoagulant salts; and (4) the difference in response of RBC to ionized and non-ionized species. Considering the complexity of the chemical processes involved, it is appropriate to consider the data developed as an empirical description rather than an exact quantitative expression. They are, nonetheless, consistent with the notion that the effects of the $Na^+$ and $K^+$ salts of EDTA on the PCV are primarily osmotic in nature.

The osmotically balanced anticoagulant compositions of the present invention are based on the surprising discovery that $H_4$ EDTA raises hematocrit values and on using this property to affect the lowering of hematocrit values by other salts in the composition. The raising of hematocrit values by $H_4$ EDTA is not believed to have been previously reported by others, and is a quite unusual property which is believed shared only by ammonium oxalate. Thus, the presence of $H_4$ EDTA is essential to the operability of the present invention.

In determining the first approximation of the ratio of $H_4$ EDTA to be used with a given salt for a particular mammalian blood species, the following technique can be employed and the resultant ratio modified if desired by simple trial and error to give hematocrit values identical to those of fresh or heparanized blood. $H_4$EDTA and the appropriate salt, e.g. $K_3$ EDTA, $Na_2$ EDTA, etc. are added separately to blood samples in the usual porportions, e.g. of 1, 2, 5 or 10 mg/ml. Hematocrit values are determined by centrifugation and plotted graphically as a percent of control hematocrit value versus concentration. The relative effects are compared and, for the linear portion of the graph, the ratio of $H_4$ EDTA effect to the salt effect on hematocrit (each as a percentage difference from the control, valued at one hundred percent) is calculated to give a constant, K. For example, if a concentration of 1 mg/ml:

Heparin hematocrit = 100%
$H_4$ EDTA hematocrit = 108% (+8%)
$K_3$ EDTA hematocrit = 97% (−3%),
Ratio = 8/3 = 2.67 = K With X being the concentration of $H_4$ EDTA, Y being the concentration of the salt and Z being the total anticoagulant concentration desired, then $X + Y = Z$ and Y=KX. Therefore, $$X + KX = Z;$$

$$X(1 + K) = Z$$

and $$X = Z/(1 + K)$$

Similarly, $Y = Z - Y$; and therefore $Y = Z - Z/(1 + K)$

Applying the formula to the above example to extrapolate for a total desired concentration of 2 mg/ml:

$$X = (Z/1 + K) = 2/3.67 = 0.54 \text{ mg/ml } H_4 \text{EDTA}$$

$$Y = Z - (Z/1 + K) = 2 - (2/1 + 2.67) = 1.46$$
$$\text{mg/ml } K_3 \text{ EDTA}$$

for a weight ratio of $K_3$ EDTA: $H_4$ EDTA of about 3:1. This ratio is substantially constant over commonly employed concentration ranges and can accordingly be used for different concentrations. If the hematocrit value of the mixture is too low as compared to the control, additional $H_4$ EDTA and/or less salt can be employed and the first approximation ratio recalculated accordingly. If too high, less $H_4$ EDTA and/or more salt can be similarly employed.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Rabbit blood was obtained by cardiac puncture under general anesthesia. All other blood samples were obtained by percutaneous venipuncture without anesthesia either into heparinized syringes (10 units/ml) or directly into commercially available "Vacutainer" blood collection tubes. Canine and feline samples were drawn from the jugular vein and human samples from the antecubital vein. All subjects appeared in good health. Packed cell volume determinations in our laboratory were performed in duplicate using a standard centrifuge. Hemoglobin (Hb) was determined colorimetrically by the cyanmethemoglobin method. Estimation of plasma protein (PP) was by index of refraction using a Goldberg refractometer. Plasma for protein determinations was obtained by breaking the capillary tubes used for the PCV determinations and expelling the plasma into the chamber of the refractometer. Samples submitted to a commercial laboratory were analyzed using a Coulter Counter Model S.

Many types of blood collecting tubes containing anticoagulants are commercially available. Some are characterized in Table 1 along with our own formulation; two (3204 QS and 3404 XF435) were supplied to us by the commercial laboratory at different times. In experiments I and II, no heparin was added to the blood. In experiments III—V, blood was drawn in heparinized blood syringes and the PCV of the heparinized blood was taken as the control value. Thus, PCV values are reported as percent of control and refer to the heparinized samples as 100% in order to facilitate comparison of results using samples from various subjects on different occasions. Likewise, in experiments where varying amounts of blood were added to commercially available tubes or where such tubes were prepared in our laboratory, the concentration of anticoagulant is indicated in terms of percent of full draft where 100% represents the full amount of blood intended for that tube. The numerical value of concentration or volume of blood can be deduced from Table 1; in this way different tubes or formulations may be more easily compared.

Experiment I: A full draft of blood was taken in two types of anticoagulant tubes (3204 QS and 3204 XF435) from 6 dogs, and PCV, Hb and PP were determined in our laboratory immediately and after 4 hr. "incubation" at room temperature.

Experiment II: The same sampling procedure was followed for 5 dogs, and the samples were submitted to the commercial laboratory. PCV, Hb, and RBC count were reported using the electronic counter.

Experiment III: Using the same two types of tubes (3204 QS and 3204 XF435), heparinized blood was added in amounts varying from 10% to 100% of full draft of the tubes. Blood from 5 dogs was used at all concentrations and the PCV's measured in our laboratory, were computed as percent of control with reference to heparinized blood of the same dog; the results were averaged for each concentration.

Experiment IV: A mixture (Formula 3) was prepared in powder form containing $H_4$ EDTA and $Na_2$ EDTA in amounts calculated to be equal and opposite in osmotic effect on the canine RBC and which should have sufficient EDTA activity to provide anticoagulation for 5 ml. of blood (1 mg $H_4$ EDTA and 8 mg $Na_2$ EDTA). Multiples of this amount ($1x$ to $10x$) were added to 5 ml. samples of heparinized canine blood in order to simulate the addition of decreasing amounts of blood to coagulant analogous to experiment III. Samples from 5 dogs were used at all concentrations and the results were treated as in experiment III.

Experiment V: On various occasions, heparinized samples of canine blood were added to several types of tubes to full draft. Single samples of human, feline and rabbit blood were treated similarly. The PCV was determined in our laboratory and reported as percent of control with reference to the original heparinized sample of the same blood.

The results of experiments I and II are shown in Table 2. The samples measured in our laboratory had PCV and PP values 10% higher when collected in 3204 XF435 tubes than in 3204 QS tubes ($P < .001$ for both). Heomglobin measurements were not significantly affected by choice of tubes ($P > 0.4$). With incubation of 4 hr. Hb values increased in both tube types ($P < .001$); but the PCV remained essentially unchanged ($P > 0.4$).

Table 2 also shows the results obtained when comparable blood samples were analyzed at the commercial laboratory (using the electronic counter). There was no significant difference in any of the hematologic values referable to the choice of tube and anticoagulant.

The results of experiments III and IV can be seen in Table 5. As may be seen, with increasing concentration of $K_3$ EDTA (tube type 3204 QS) the PCV decreased in a manner which might have been anticipated (2—2). With increasing concentrations of $H_4$ EDTA (tube type 3204 XF435), PCV increased monotonically. With the balanced anticoagulant mixture (Formula 3), the PCV was independent of anticoagulant concentration over a wide range.

Table 1 lists the effect of various anticoagulant and concentrations on the PCV with full draft of canine blood. Table 3 shows similar date for other species.

The osmotically balanced anticoagulant mixture of the present invention was additionally compared with widely employed $K_3$ EDTA for possible effects on other routine hematology tests including red blood cells, white blood cells, hematocrit and hemoglobin values. The lack of any significant variation in the results obtained is apparent from the test results shown in Table 4.

TABLE 1

Effect of different types of collection tubes containing different anticoagulants on PCV of canine blood

| Tube type | Anticoagulant | Amount Per Tube | Draft | No. Samples | Mean PCV as % of control |
| --- | --- | --- | --- | --- | --- |
| 3272 QS | $K_3$ EDTA | 7.5 mg (.05 ml of 15%) | 2 ml | 6 | 93.5 |
| 3204 QS | $K_3$ EDTA | 9 mg (.06 ml of 15%) | 7 ml | 30 | 98.0 |
| 3206 XF220 | $K_3$ EDTA | 4 mg (.04 ml of 10%) | 3 ml | 6 | 93.6 |
| 3204 Q | $Na_2$ EDTA | 9 mg | 9 ml | 6 | 98.2 |
| 3204 XF435 | $H_4$ EDTA | 7 mg | 5 ml | 30 | 104.3 |
| 3204 NAX | Na Oxalate | 67 mg (0.5 ml of 0.1 M) | 5 ml | 6 | 90.1 |
| Formula 3 | $H_4$ EDTA $Na_2$ EDTA | 1 mg 8 mg | 5 ml | 12 | 99.6 |
| Control | Heparin | 10u/ml | | | 100 |

TABLE 2

Comparison of two types of collection tubes containing different anti-coagulants on canine blood values

| Tube type | No. samples | Hemoglobin Mean | Hemoglobin SD | PCV Mean | PCV SD | Plasma Protein Mean | Plasma Protein SD | RBC ($\times 10^6$) Mean | RBC ($\times 10^6$) SD |
|---|---|---|---|---|---|---|---|---|---|
| *Tested Immediately* | | | | | | | | | |
| 3204 QS | 6 | 15.56 | 1.33 | 47.2 | 3.16 | 7.00 | 0.55 | N/D[a] | N/D |
| 3024 XF435 | 6 | 15.46 | 1.04 | 52.3 | 4.46 | 7.75 | 0.63 | N/D | N/D |
| *Tested After 4 Hour Incubation* | | | | | | | | | |
| 3204 QS | 6 | 16.25 | 1.09 | 47.2 | 2.74 | 6.97 | 0.52 | N/D | N/D |
| 3204 XF435 | 6 | 16.15 | 1.23 | 51.8 | 3.80 | 7.90 | 0.70 | N/D | N/D |
| *Tested in Commercial Laboratory* | | | | | | | | | |
| 3204 QS | 5 | 15.16 | 1.58 | 41.0 | 5.00 | N/D | N/D | 6.00 | 0.64 |
| 3204 XF435 | 5 | 15.30 | 1.60 | 41.2 | 3.00 | N/D | N/D | 6.00 | 0.78 |

[a] N/D = not done

TABLE 3

Effect of various tubes containing different anticoagulants on PCV of human, rabbit and feline blood

| Tube type | Human PCV (% of control) | Rabbit PCV (% of control) | Feline PCV (% of control) |
|---|---|---|---|
| Control (Heparin) | 48.0 (100%) | 35.0 (100%) | 30.5 (100%) |
| 3204 Q | Not Done | 33.5 (95.7%) | 29.5 (96.7%) |
| 3204 NAX | 43.0 (89.6%) | 31.0 (88.6%) | 27.5 (90.2%) |
| 3204 XF435 | 52.0 (108.3%) | 39.0 (111.4%) | 35.0 (114.7%) |
| 3204 QS | 47.0 (97.9%) | 34.0 (97.2%) | 30.0 (98.4%) |
| 3272 QS | 46.5 (96.9%) | 32.0 (91.4%) | 29.0 (95.1%) |

TABLE 4

| Tube Type | RBC $\times 10^6$ Mean | RBC $\times 10^6$ S.D. | WBC $\times 10^3$ Mean | WBC $\times 10^3$ S.D. | HCT % Mean | HCT % S.D. | HB Gms% Mean | HB Gms% S.D. |
|---|---|---|---|---|---|---|---|---|
| $K_3$ EDTA | 6.51 | 0.65 | 10.94 | 3.31 | 46.5 | 5.1 | 16.22 | 2.14 |
| Formula 3 | 6.39 | 0.58 | 11.01 | 3.11 | 46.9 | 5.5 | 16.38 | 2.03 |
| t | .09942 | | 0.3371 | | 0.7513 | | 1.2027 | |
| p | > 0.3 | | > 0.7 | | > 0.4 | | > 0.25 | |

HEMATOLOGIC PARAMETERS OF CANINE BLOOD
(n = 10 Samples)

TABLE 5

| | | | | | |
|---|---|---|---|---|---|
| $K_3$ EDTA conc., mg/ml | 1.3 | 1.8 | 2.98 | 9.2 | 18.4 |
| HCT, % of control | 97.6 | 95.4 | 93.3 | 83.0 | 80.0 |
| $H_4$ EDTA conc., mg/ml. | 1.40 | 2.33 | 3.50 | 7.0 | 14.0 |
| HCT, % of control | 106.9 | 112.4 | 113.9 | 117.8 | 121.5 |

While exemplified principally with reference to canine blood, it will be apparent that the anticoagulant mixture of the present invention is suitable for use with any blood containing osmotically sensitive erythrocytes such as that of humans; laboratory animals, e.g. rabbits, mice, rats, monkeys, hamsters, cats, etc.; and as veterinary animals, e.g. cattle, horses, pigs, sheep, goats, etc. Substances which do not deleteriously effect the osmotic balance may if desired also be included, such as is conventional in blood chemistry, e.g. sorbic acid, sodium azide or other preservatives, etc.

The preceding examples can be repeated with similar success by substituting the generically or specifically described components and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a composition of matter comprising in vitro whole mammalian blood in admixture with an effective amount of an anticoagulant, the improvement wherein the anticoagulant is an osmotically balanced composition consisting essentially of (a) $H_4$ EDTA in free acid form and (b) at least one salt which lowers hematocrit values as determined by centrifugation, the ratio of (a) : (b) being such that said hematocrit values of the blood are substantially identical to those of fresh or heparinized blood and substantially independent of the concentration of said composition.

2. A composition according to claim 1, wherein (b) is at least one alkali metal salt of EDTA.

3. A composition according to claim 2, wherein said salt is $Na_2$ EDTA, $K_3$ EDTA or a mixture thereof.

4. A composition according to claim 3, wherein the weight ratio of $a : b$ is 1:1 to 2:20.

5. A composition according to claim 4, wherein said ratio is 1:1 to 1:20.

6. A composition according to claim 1, wherein the concentration of $H_4$ EDTA is 0.1 - 10 mg/ml.

7. A composition according to claim 6, wherein said concentration is about 0.5 - 5 mg/ml.

8. A composition according to claim 1, wherein said blood is human blood.

9. A composition according to claim 8, wherein the concentration of $H_4$ EDTA is 0.1 - 10 mg/ml; component (b) is $Na_2$ EDTA, $K_3$ EDTA or a mixture thereof; and the weight ratio of (a) : (b) is 1:1 to 1:20.

10. An osmotically balanced anticoagulant for in vitro use with whole mammalian blood, which comprises an anticoagulantingly effective amount of a balanced EDTA salt composition consisting essentially of (a) $H_4$ EDTA and (b) a salt which lowers hematocrit values, the molar ratio of (a) : (b) being such that the hematocrit values of the blood sample are substantially identical to those of fresh or heparinized blood and substantially independent of the concentrations of (a) and (b).

11. In a method for collecting a blood sample to be used in hematological testing which comprises drawing a whole blood sample into a collection tube containing an anticoagulant, the improvement wherein said anticoagulant is the composition according to claim 10.

12. In a blood collection tube containing an anticoagulant, the improvement wherein said anticoagulant is the composition according to claim 10.

* * * * *

UNITED STATES PATENT AND TRADEMARK OFFICE
CERTIFICATE OF CORRECTION

PATENT NO. : 4,090,977
DATED : May 23, 1978
INVENTOR(S) : Stephen Dubin

It is certified that error appears in the above-identified patent and that said Letters Patent are hereby corrected as shown below:

Claim 4, line 2: "2:20" should be --- 1:20 ---.

Claim 5, line 2: "1:1 to 1:20" should be --- 1:2 to 1:10 ---.

Claim 9, line 4: "1:1 to 1:20" should be --- 1:2 to 1:10 ---.

*Signed and Sealed this*

*Twenty-first* Day of *November 1978*

[SEAL]

*Attest:*

RUTH C. MASON
*Attesting Officer*

DONALD W. BANNER
*Commissioner of Patents and Trademarks*